United States Patent [19]

Stetter et al.

[11] Patent Number: 4,693,980

[45] Date of Patent: Sep. 15, 1987

[54] NEW TYPE II RESTRICTION ENDONUCLEASE MAE III, A PROCESS FOR OBTAINING IT AND THE USE THEREOF

[75] Inventors: Karl O. Stetter, Regensburg; Rüdiger Schmitt, Niedergebraching/Pentling; Frank Laue, Pähl, all of Fed. Rep. of Germany

[73] Assignee: Boehringer Mannheim GmbH, Mannheim-Waldhof, Fed. Rep. of Germany

[21] Appl. No.: 655,470

[22] Filed: Sep. 28, 1984

[30] Foreign Application Priority Data

Jan. 18, 1984 [DE] Fed. Rep. of Germany ....... 3401620

[51] Int. Cl.⁴ .................. C12N 9/22; C12N 9/16; C12N 15/00; C12R 1/01
[52] U.S. Cl. .................................. 435/199; 435/196; 435/172.3; 435/822
[58] Field of Search ............... 435/195, 196, 199, 822, 435/91, 172.3

[56] References Cited

PUBLICATIONS

Schmid, K. et al., *Nuc. Acids Res*, vol. 12, No. 6, pp. 2619–2628, Mar. 1984.
Balch, W. et al., *Micro. Reus*, vol. 43, No. 2, pp. 260–264, 285 and 286, 1979.

*Primary Examiner*—Thomas G. Wiseman
*Assistant Examiner*—Jayme A. Huleatt
*Attorney, Agent, or Firm*—Felfe & Lynch

[57] ABSTRACT

The present invention provides a restriction endonuclease, characterized by the palindromic recognition sequence:

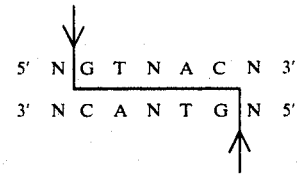

and the cleavage position defined by the arrows.

The present invention also provides a process for obtaining this new restriction endonuclease.

6 Claims, No Drawings

NEW TYPE II RESTRICTION ENDONUCLEASE MAE III, A PROCESS FOR OBTAINING IT AND THE USE THEREOF

The present invention is concerned with a new Type II restriction endonuclease MaeIII, with a process for obtaining it and with the use thereof.

Type II restriction endonucleases are endodeoxyribonucleases which are able to recognize and cleave certain DNA at nucleotide sequences. Phosphodiester bridges are thereby hydrolysed in the target sequence, namely one in each polynucleotide chain. Therefore, Type II restriction endonucleases are valuable for the analysis of DNA molecules.

Specific Type II restriction endonucleases are admittedly already known for numerous recognition sequences, but there is still a need for the provision of further Type II restriction endonucleases which are specific for such recognition sequences for which restriction endonucleases have not been recognized.

Therefore, it is an object of the present invention to provide a new restriction endonuclease which is able specifically to recognize and cleave a sequence which hitherto have not been recognized by any such enzyme.

Thus, according to the present invention, there is provided a restriction endonuclease which is characterized by the palindromic recognition sequence:

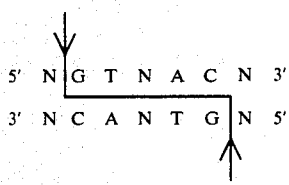

and the cleavage position defined by the arrows.

The new Type II restriction endonuclease according to the present invention, which in the following is called MaeIII, has a temperature optimum of 45 to 48° C. and a pH optimum at 8.0/45° C. in Tris/HCl buffer. Further optimum reaction parameters are 350 mM NaCl, 10 to 18 mM $Mg^{2+}$, 0 to 20 mM 2-mercaptoethanol. The presence of magnesium ions is essential for the activity of the enzyme.

As mentioned above, the enzyme acts upon palindromic structures and thus recognizes a self-complementary structure in which the complementary strand of the DNA has the identical sequence in the opposite-running direction.

The recognition sequence and the point of cleavage of the enzyme can be ascertained as follows: the plasmid pBR322 is completely digested with HinfI. The HinfI fragments B and C (517 bp and 506 bp, respectively) are isolated, their 3'-ends are marked with alpha-[$^{32}$P] dATP and Klenow polymerase and subsequently cleaved with AluI. From the marked fragments which hereby results, there is isolated and sequenced the 330 bp fragment (pBR322, position 3037 to 3366, length of the fragment including single strand ends).

An aliquot of the 330 bp fragment is cleaved with the enzyme according to the present invention resulting in two fragments. The cleavage position 3293 lying close to the 3'labeled end was determined.

The length of the HinfI/MaeIII fragment is determined in sequence gels. The HinfI/MaeIII fragment thereby runs in the gel like the "A" in the sequence ladder which stands 5'-adjacent to the recognition sequence 5'-GTNAC-3'. Therefore, it terminates with the nucleotide G of the recognition sequence. The cleavage point of MaeIII is thus 5'-positioned to the 5'-flanking nucleotide G.

The new endonuclease MaeIII is obtained, according to the present invention, by culturing *Methanococcus aeolicus* DSM 2835 and recovering the enzyme from the cells. For the recovery, there can be used conventional biochemical purification methods, whereby, in each of the fractions obtained, the presence of the enzyme can be demonstrated on the basis of the cleavage of its recognition sequence. As substrate, there can be used for example, pBR322-DNA. The DNA fragments obtained are separated electrophoretically in agarose gels in the buffer systems conventional for fragment separation in the presence of ethidium bromide.

The microorganism used for obtaining the enzyme grows anaerobically in Medium III (Microbiol. Reviews, 43, 260–296/1979) on $H_2/CO_2$ or on formate. It forms regular to irregular cocci of about 2 μm diameter, individually and in pairs. On agar, there are formed round, convex, pale ochre-coloured colonies of about 2 mm diameter. The microorganism is gram-negative. The cell integument consists of protein subunits. Growth takes place at a temperature of from 25° to 50° C., the temperature optimum being 45° C. (2 hours duplication time). Growth takes place in the presence of 1.5 to 5% and optimally of 4% sodium chloride. The DNA base composition is about 28.6% G+C. Therefore, the microorganism differs from the known Methanococci by a somewhat lower GC content of the DNA, by the optimal growth temperature of 45° C., by the markedly larger cells and by the presence of new restriction enzymes. *Methanococcus aeolicus* has been deposited at the Deutsches Sammlung von Mikroorganismen, Gesellschaft für Biotechnologische Forschung GmbH, Grisebachstrasse 8, 3400 Göttingen, Federal Republic of Germany, and bears Accession Number DSM 2835.

In a preferred embodiment of the process according to the present invention, the cells are digested, the extract is mixed with polyethyleneimine up to a concentration of 0.65%, the precipitate is separated off and from the supernatant there is obtained the fraction precipitating out between 60 and 95% ammonium sulphate saturation.

For the digestion, there can be used the conventional mechanical and chemical methods, for example high pressure dispersion, ultrasonics or enzymatic digestion.

Further purification of the ammonium sulphate fraction containing the new enzyme is preferably conducted by molecular sieve fractionation, chromatography over anion exchangers and over cation exchangers, as well as final affinity chromatography. As molecular sieve material, there has proved to be useful the product which is commercially available under the designation Ultrogel AcA 34, this being an acrylamide/agarose heteropolymer of 3% acrylamide and 4% agarose. As anion exchangers, there can be used carrier materials based on sepharose, cellulose or synthetic polymers which are modified with diethylaminoethyl substituents, for example the products of Pharmacia, Uppsala, Sweden, which are commercially available under the designation DEAE-Sephacel.

As cation exchangers, there are preferably used phosphate group-containing substances, preferably carbohydrates, for example cellulose phosphate and the like. For the affinity chromatography, carrier-fixed heparin, for example heparin-sepharose, has proved to be especially useful.

The following examples are given for the purpose of illustrating the present invention:

EXAMPLE 1

*Methanococcus aeolicus* DSM 2835 is allowed to grow anaerobically at 45° C. for 3 days in minimal formate medium, which is described in detail hereinafter, whereafter it is harvested in the stationary phase. 35 g of the cell paste so obtained are suspended in 70 ml digestion buffer (40 mM Tris/HCl, pH 8.0/4° C.; 0.1 mM EDTA (ethylenediamine-tetraacetic acid); 7 mM 2-mercaptoethanol and 0.2 mM PMSF (phenylmethanesulphonyl fluoride). The cells are then digested twice by high pressure dispersion in a precooled pressure cell at 1100 bar = 16,000 PSI.

To the digestion suspension ammonium chloride is added to a final concentration of 0.3M. Subsequently, 7 ml of a 10% polyethyleneimine solution are added to give a final concentration of 0.65% (v/v). After leaving to stand for 30 minutes at 4° C., the precipitate formed is centrifuged off for 60 minutes at 27,300 g or 23,000 g and discarded. The supernatant is mixed with solid ammonium sulphate up to 60% saturation, left to stand for 2 hours at 4° C. and then centrifuged off for 60 minutes at 27,300 g or 23,000 g. The resultant supernatant is again brought to 90% saturation with sold ammonium sulphate. After 16 hours at 4° C., the ammonium sulphate precipitate is centrifuged off for 60 minutes at 27,300 g and further worked up.

The minimal medium referred to above has the following composition:

| dissolve: | g/liter |
| --- | --- |
| KCl | 0.32 g |
| $MgCl_2.6H_2O$ | 2.75 g |
| $MgSO_4.7H_2O$ | 3.45 g |
| $NH_4Cl$ | 0.25 g |
| $CaCl_2.2H_2O$ | 0.15 g |
| $K_2HPO_4$ | 0.15 g |
| NaCl | 18 g |
| mineral elixir (see below) | 10 ml |
| $Fe(NH_4)_2(SO_4)_2.7H_2O$ | 2 mg |
| $NaHCO_3$ (added at end) | 5.5 g |
| resazurin 0.1% | 1 ml |
| sodium formate | 15 g |
| sodium tungstate | 3.3 mg | add 50 ml of reducing agent, consisting of 12.5 g/liter sodium sulphide, while allowing nitrogen to bubble through, 75 ml freshly prepared 1N sodium hydroxide solution and 1 ml 0.1% resazurin, adjust the pH value with formic acid to 6.9, make up to 1 liter and allow nitrogen to bubble through.

The mineral elixir referred to above has the following composition:

| | g/liter |
| --- | --- |
| Titriplex I | 1.5 g |
| $MgSO_4.7H_2O$ | 3.0 g |
| $MnSO_4.2H_2O$ | 0.5 g |
| NaCl | 1.0 g |
| $FeSO_4.7H_2O$ | 0.1 g |
| $CoSO_4$ or $CoCl_2$ | 0.1 g |
| $CaCl_2.2H_2O$ | 0.1 g |
| $ZnSO_4$ | 0.1 g |

| | g/liter |
| --- | --- |
| $CuSO_4.5H_2O$ | 0.01 g |
| $KAl(SO_4)_2$ | 0.01 g |
| $H_3BO_3$ | 0.01 g |
| $Na_2MoO_4.2H_2O$ | 0.01 g |
| slowly adjust pH value to 6.5 with 5 N KOH | |

EXAMPLE 2

The ammonium sulphate precipitate obtained according to example 1 is taken up with TEMG buffer (40 mM Tris/HCl, pH 8.0/4° C.; 0.1 mM EDTA; 7 mM 2-mercaptoethanol; 10% v/v glycerol) and 0.5M sodium chloride solution and applied to an Ultrogel AcA-34 molecular sieve column of 3×100 cm. This column is eluted with TEMG buffer +0.5M sodium chloride solution and the eluate fractions with MaeIII activity are combined.

The combined eluate fractions are chromatographed on an anion exchanger column (DEAE-Sephacel; 2×10 cm) equilibrated with TEMG buffer. After washing with 2 column volumes of TEMG buffer, the enzyme is eluted with a linear gradient of 0 to 1M sodium chloride in TEMG. The enzyme appears in the fractions with 0.1 to 0.15M sodium chloride. The active fractions are combined and dialysed against TEMG buffer. The dialysate is chromatographed on a cation exchanger column (cellulose phosphate P 11; 1×10 cm) equilibrated with TEMG buffer. Washing and elution take place as in the case of the anion exchanger column. MaeIII is eluted between 0.55 and 0.65M sodium chloride. The combined enzyme-containing fractions are again dialysed against TEMG buffer and the dialysate chromatographed over an affinity chromatography column (heparin-sepharose CL-6B; 1×5 cm) equilibrated with TEMG buffer. Washing and elution again takes place as described in the case of the anion exchanger column. MaeIII is eluted between 0.65 and 0.85M sodium chloride. The active fractions are combined and dialysed against 20 mM Tris/HCl buffer, pH 8.0, 4° C., containing 0.1 mM EDTA, 10 mM 2-mercaptoethanol, 100 mM sodium chloride, 50 vol.% glycerol, 0.01 vol.% Triton X100, and stored at −20° C. The activity is about 100 U MaeIII (definition of activity: 1 U=1 µg pBR322-DNA/hour at 45° C. completely cleaved).

Determination of activity

Into a mixture of 5 µl incubation buffer, containing 0.03M Tris/HCl, pH 8.0/45° C., 1.75M sodium chloride, 0.07M magnesium chloride, 0.035M 2-mercaptoethanol and 0.05 vol.% Triton X100, there are introduced 14 µl water and 5 µl pBR322-DNA (4 OD/ml), as well as 1 µl MaeIII solution (1 U/µl). The solution is maintained at 45° C. for 1 hour, cooled on ice and mixed with 5 µl cold stop solution, containing 7M urea, 20% w/v sucrose, 0.06M EDTA and 0.01% w/v bromophenol blue. It is then separated electrophoretically on 1% agarose gel for 3 to 4 hours at 100 V. The bands obtained are identified in comparison with suitable DNA length standards.

We claim:

1. A restriction endonuclease capable of recognizing and cleaving a DNA sequence at a position indicated by the arrows

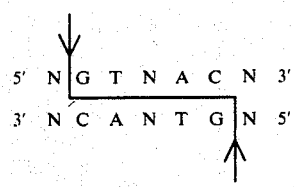

2. The restriction endonuclease of claim 1 wherein said endonuclease is characterized by a temperature optimum between 45° and 48° C. and a pH optimum at 8.0/45° C. in Tris HCl buffer.

3. A process for obtaining the restriction endonuclease of claim 1 comprising the steps of culturing *Methanococcus aeolicus* DSM 2835 cells and recovering the restriction endonuclease from the cells.

4. The process of claim 3 comprising recovering the endonuclease from the cells of *Methanococcus aeolicus* by digesting the cells to release an extract therefrom, mixing the extract released from the digested cells with polyethylenimine up to a concentration of 0.65% v/v, separating off insolubles and leaving a supernatant, mixing the supernatant with ammonium sulphate in an amount of up to 60 to 95% saturation to form a precipitated fraction and recovering the precipitated fraction.

5. The process of claim 4, further comprising purifying the ammonium sulphate precipitated fraction by at least one process selected from the group consisting of molecular sieve fractionation, chromatography over a weakly basic anion exchanger, chromatography over a weakly acidic cation exchanger, and affinity chromatography.

6. The process of claim 5, wherein carrier-fixed heparin is used for the affinity chromatography.

* * * * *